United States Patent [19]

Hansen et al.

[11] Patent Number: 5,179,079
[45] Date of Patent: Jan. 12, 1993

[54] NASAL FORMULATION AND INTRANASAL ADMINISTRATION THEREWITH

[75] Inventors: Philip E. Hansen, Copenhagen; Anders R. Sorensen, Herlev, both of Denmark

[73] Assignee: Novo Nordisk A/S, Bagsvaerd, Denmark

[21] Appl. No.: 819,141

[22] Filed: Nov. 27, 1991

Related U.S. Application Data

[63] Continuation of Ser. No. 172,409, Mar. 24, 1988, abandoned.

[30] Foreign Application Priority Data

Dec. 16, 1986 [DK] Denmark .............................. 6042/86
Jul. 16, 1987 [DK] Denmark .............................. 3700/87

[51] Int. Cl.$^5$ .................. A61K 37/02; A61K 37/26; A61K 31/66; A61K 9/10
[52] U.S. Cl. ........................... 514/4; 514/866; 514/884; 514/946; 514/947; 514/950; 514/951; 514/952; 514/943; 514/970
[58] Field of Search ............. 514/4, 866, 884, 946, 514/947, 950–951, 952, 943, 970

[56] References Cited

U.S. PATENT DOCUMENTS

| | | | |
|---|---|---|---|
| 3,594,476 | 7/1971 | Merrill | 514/78 |
| 3,869,549 | 3/1975 | Geller | 514/805 |
| 4,153,689 | 5/1979 | Hirai et al. | 514/3 |
| 4,476,116 | 10/1984 | Anik | 514/15 |
| 4,548,922 | 10/1985 | Carey et al. | 514/171 |
| 4,614,730 | 9/1986 | Hansen et al. | 514/3 |
| 4,617,149 | 10/1986 | Dimarchi et al. | 530/324 |
| 4,944,948 | 7/1990 | Uster et al. | 424/450 |
| 5,023,087 | 6/1991 | Yau-Young | 424/450 |

FOREIGN PATENT DOCUMENTS

| | | |
|---|---|---|
| 988852 | 5/1976 | Canada . |
| 0084341 | 7/1983 | European Pat. Off. . |
| 0100964 | 7/1983 | European Pat. Off. . |
| 0111841 | 12/1983 | European Pat. Off. . |
| 0128831 | 12/1984 | European Pat. Off. . |
| 0160501 | 11/1985 | European Pat. Off. . |
| 0130550 | 12/1986 | European Pat. Off. . |
| 0200383 | 12/1986 | European Pat. Off. . |
| 0219896 | 4/1987 | European Pat. Off. . |
| 0257454 | 3/1988 | European Pat. Off. . |
| WO85/05029 | 11/1985 | PCT Int'l Appl. . |
| WO86/04233 | 7/1986 | PCT Int'l Appl. . |
| 636011 | 5/1983 | Switzerland . |
| 1527605 | 10/1978 | United Kingdom . |
| 2107985 | 5/1983 | United Kingdom . |
| 2150433 | 7/1985 | United Kingdom . |

OTHER PUBLICATIONS

Robert Salzman et al., "Intranasal Aerosolized Insulin", The New England Journal of Medicine, Apr. 25, 312:1078–1084, (1985).
Robert E. Stratford, Jr. et al., "Aminopeptidase activity in homogenates of various absorptive mucosae in the albino rabbit: implications in peptide delivery", International Journal of Pharm. 30 (1986) pp. 73–82.
Fritz Paltauf, "Chemical Synthesis of Ester Lipids", Academic Press, Inc. (1983) pp. 520–526.
E. Cubero Robles et al., "Synthesis of Lecithins by Acylation of O-(in-Glycero-3-Phosphoryl)Choline with Fatty Acid Anhydride", Biochemica et Biophysica Acta; 187(1969) pp. 520–526.
Lisbeth Illum, "Drug delivery systems for nasal application," Arch. Pharm. Chemi. 94, (1987), pp. 127–135.
Derwent Abstract No. C84–003184 of Jp58201712, Nov. 1983; English language abstract.
The Merck Index, 9th edition, Merck and Co. Inc., Rahway, N.J., (1976) entry Nos. 4277, 4815, 4859 on pp. 573, 652 & 659.

*Primary Examiner*—Ronald W. Griffin
*Attorney, Agent, or Firm*—Fidelman & Wolffe

[57] ABSTRACT

The systemic absorption after intranasal administration of certain drugs, in particular pharmacologically active polypeptides is enhanced in the presence of a phospholipid, such as a phosphatidylcholine (a lecithin), preferably admixed with a vegetable oil.

17 Claims, No Drawings

NASAL FORMULATION AND INTRANASAL ADMINISTRATION THEREWITH

CROSS REFERENCE TO RELATED APPLICATION

This Application is a continuation of Ser. No. 07/172,409, filed Mar. 24, 1988, now abandoned.

The present invention relates to novel pharmaceutical preparations adapted for intranasal administration and to a process for preparing such preparations.

BACKGROUND OF THE INVENTION

While non-invasive medication, such as oral or rectal administration of a drug is undoubtedly most convenient to the patient, parenteral drug delivery is usually regarded as being the most effective. In particular, drugs which are inactivated in or poorly absorbed by the gastrointestinal tract and drugs which are subject to extensive first pass hepatic metabolism following oral administration are usually administered parenterally.

There are obvious inconveniences associated with parenteral drug administration, such as the need for sterile delivery devices, pain and irritation caused by reiterated injections and the potential risk of infection. Therefore, alternative means of drug delivery, equalling parenteral administration in the sense that first pass metabolism is circumvented, have been sought. One such potentially promising alternative is drug administration via the nasal route. However, just as is the case with other methods for non-invasive medication, the bioavailability of a drug after intranasal administration is largely, unpredictable, depending inter alia on the chemical nature of the drug.

Thus it is known that progesterone and propranolol are absorbed from the nasal cavity in a manner providing blood levels almost equal to intravenous administration.

Other examples of intranasal formulations of pharmaceutically active agents with molecular weights up to about 1 kD are known, for example compositions containing ergopeptide alkaloids dissolved in aqueous ethanol administered as aerosols (Swiss Patent No. 636,011), salts of pharmaceutically active amines with fatty acids (Canadian Patent No. 988,852) and catecholamine suspended in a fatty acid (or ester) emulsified with polyoxyethylene (European Patent Publication No. 0 160 501 A).

Over the last decades a variety of (mainly synthetic) polypetide drugs have been developed. In general, polypeptides have been administered parenterally due to incomplete absorption from and digestive instability in the alimentary canal. This is probably the reason why in particular studies of the nasal delivery of polypeptides have been intensified during recent years. It has been found that while some smaller polypeptides (up to about 10 amino acid residues) may be reasonably well absorbed intranasally from simple aqueous formulations, generally the nasal bioavailability of larger polypeptides becomes both incomplete and variable, and increasingly so with increasing molecular weight (for review, see L. Illum: Archiv for Pharmaci og Chemi 94 (1987), 127-135).

With a view to overcoming the disadvantages encountered particularly with nasal delivery compositions containing larger polypeptides, the additional incorporation of a variety of biocompatible absorption promoting agents or so-called enhancers has been devised.

In this respect reference is made to European Patent Publication No. 0 111 841 A, disclosing the absorption enhancing effect of a bile acid and to U.S. Pat. No. 4,476,116, using chelating agents such as EDTA.

Nasal formulations adapted to insulin delivery would naturally be highly preferred by the insulin dependent diabetic patient to the presently available preparations for parenteral administration provided that the insulin is absorbed to a reasonably effective and constant extent from the nasal cavity. A variety of absorption enhancing agents, mainly surfactants, have been devised for such formulations.

Ionic as well as non-ionic surfactant enhancers, such as bile acid salts and polyoxyethylene higher alcohol ethers are disclosed in British Patent No. 1,527,605 while the use of a specific polyoxyethylene higher alcohol ether, namely polyoxyethylene-9 lauryl ether is described in: R. Salzman et al., New England J. of Med. 312 (1985), 1078-1084. Other enhancers, for example salts of taurodihydrofusidic acid, are disclosed in U.S. Pat. No. 4,548,922.

The chemical structure of enhancers known heretofore deviate considerably from those of known constituents of cellular membranes, including those of the nasal cavity. This feature could possibly explain their general proneness to cause nasal irritation or even permanent damage to the nasal membrane, particularly during chronic administration. On this background enhancers more akin to other physiologically occurring surfactants, such as phospholipids could be contemplated. However, according to the data disclosed in British Patent No. 1,527,605 (supra) the phospholipids in a commonly supplied long chain lecithin mixture have no detectable absorption promoting effect in insulin containing nasal formulations.

It has now surprisingly been found that medium chain length phosphatidylcholines and phosphatidylethanolamines substantially promote the intranasal absorption of pharmaceutically active compounds, in particular of polypeptides, without damaging or irritating the nasal mucosa. The intranasal absorption is further enhanced from formulations wherein a fatty oil, for example a vegetable oil, is admixed with the phospolipid.

SUMMARY OF THE INVENTION

According to its first aspect the present invention provides a preparation for intranasal administration comprising a pharmaceuticaly active agent and an absorption enhancing system comprising at least one phospholipid of the general formula I

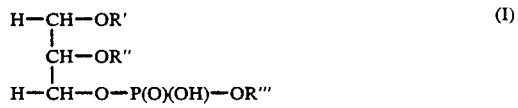

wherein R' and R" are identical or different, each selected from the group consisting of hydrogen, alkyl, alkenyl, alkylcarbonyl, alkenylcarbonyl and alkadienyl-, alkatrienyl- or alkatetraenylcarbonyl containing up to a total of 14 carbon atoms, provided that both R' and R" are not hydrogen, and R''' represents a hydrophilic moiety selected from the group consisting of 2-(trimethylammonio)ethyl, 2-aminoethyl, 2-carboxy-2-aminoethyl, 2,3-dihydroxypropyl and pentahydroxycyclohexyl, thus comprising phosphatidyl derivatives of choline (lecithins), ethanolamine, glycerol, serine and inositols, respectively. Optionally, but preferably, the absorption enhancing system also comprises a fatty oil in admixture with the phospholipid(s).

According to a second aspect of the present invention there is provided a process for making a preparation for intranasal administration, which method comprises dispersing at least one phospholipid of the general formula I, optionally, but preferably admixed with a fatty oil, in a liquid or solid diluent together with the pharmaceutically active agent either in solution or in a powdery state, which diluent may optionally comprise ancillary pH-buffering, preserving and osmotic pressure controlling agents.

PREFERRED EMBODIMENTS AND DETAILED DESCRIPTION THEREOF

A preferred subclass of compounds of formula I is compounds, wherein R' and R" are each alkylcarbonyl. A further preferred subclass of compounds of formula I is compounds, wherein R''' represents 2-(trimethylammonio)ethyl, such compounds being known as lecithins. A still further preference is for compounds of formula I, wherein R' and R" each represent alkylcarbonyl or alkyl with from about 4 carbon atoms, preferably not more than 12 carbon atoms. The most preferred subclass of compounds of formula I is compounds wherein R' and R" each represent nonylcarbonyl.

A preferred preparation of this invention is one containing a mixture of two phospholipids of formula I, preferably in proportions by weight of from 1:10 to 10:1, more preferred from 1:2 to 2:1. One of these two phospholipids may conveniently be a compound wherein R' and R" both are octanoyl, decanoyl or lauroyl. The other of these two phosphollipids may conveniently be a compound wherein one of the two substituents R' and R" is hydrogen and the other of the two substituents R' and R" is octanoyl, decanoyl or lauroyl (dodecanoyl).

Examples of preferred compounds of formula I are:
dioctanoyl L-α-phosphatidylcholine,
dioctyl-O-L-α-phosphatidylcholine,
didecanoyl L-α-phosphatidylcholine,
didecyl-O-L-α-phosphatidylcholine,
decyl-O-L-α-lysophatidylcholine
dilauroyl L-α-phosphatidylcholine,
lauroyl L-α-lysophosphatidylcholine.

The preparation of a number of compounds of formula I has been described, e.g. by E. C. Robles and D. Van Den Berg: Biochim. Biophys.Acta 187 (1969), 520–526, H. K. Mangold and F. Paltauf (Eds.) in: Ether Lipids, Chapter 3, Acad.Press 1983. Other compounds of formula I can be prepared by analogous methods.

The fatty oil optionally incorporated into the absorption enhancing system of this invention is preferably a vegetable oil, more preferably soybean oil, peanut oil, coconut oil, maize oil, olive oil, sunflower oil, or mixtures thereof.

In another preferred embodiment of this invention the pharmaceutically active agent is a polypeptide. One group of preferred polypeptides is insulin and insulin derivatives, e.g. insulin modified by chemical or enzymatic methods or by recombinant DNA technology, or mixtures of such insulins, proinsulin and glucagon. Other preferred polypeptides are parathyroid hormone, parathyroid hormone antagonist, calcitonin, vasopressin, renin, prolactin, growth hormone, thyroid stimulating hormone, corticotropin, corticotropin-releasing factor, follicle stimulating hormone, luteinizing hormone, chorionic gonadotropin, atrial peptides, interferon, tissue plasminogen activator, gammaglobulins, Factor VII, Factor VIII, growth hormone releasing hormone, luteinizing hormone releasing hormone, somatostatin and cholecystokinins.

The preparation of this invention may be liquid, e.g. adapted for administration as a spray or a solid, e.g. a powder acceptable for snuffing. Liquid preparations, such as those based on aqueous formulations, will usually include ancillary agents, for example a pH-buffering system, preferably a buffer such as phosphate, citrate or acetate buffers, a preservative and an osmotic pressure controlling agent, e.g. glycerol or sodium chloride. Powder formulations may contain the pharmaceutically active agent and the absorption enhancing system in admixture with nasally acceptable powdery diluents or mixtures thereof, e.g. cellulose or derivatives thereof, for example cellulose ethers or sodium carboxymethylcellulose, starch, a long chain fatty acid or a salt thereof, e.g. aluminum stearate, an organic polymer, e.g. of an acrylic acid derivative or inorganic vehicles, such as talc or diatomaceous earth. Supplementary addition of water-absorbing polymers, for example polyethylene glycol or polyvinyl pyrrolidone may be desirable to improve adhesion of the powder formulation to the nasal mucosa.

Preferred liquid preparations are those in which the diluent is water. Such preparations may be prepared by dispersing the absorption enhancing system in the aqueous medium containing the pharmaceutically active agent and ancillary agents, the dispersion being conducted by any method usually employed for suspension or emulsification, e.g. ultrasonic treatment. Adjustment of the aqueous phase to neutrality (i.e. to pH in the range from about 6.5 to about 8) may be accomplished in any of the preparatory steps. Preferably, microemulsions are prepared in which the size of the dispersed particles or droplets is of the order of 10 nm, thereby facilitating their passage across the nasal mucosa. Such microemulsions may be sterilized by filtration. The content of phospholipid of formula I and of fatty oil in preferred formulations of the present invention is in the range of from 0.01 to 10%, preferably from 0.5 to 5% (w/v), and 0.01–50%, preferably from 0.1 to 10% (w/v), respectively, of the preparation. Due to the fact that proteases and peptidases are associated with the nasal mucosa (see R. E. Stratford and V. H. L. Lee: Int. Journ. Pharmaceutics 30 (1986), 73–82) it may be desirable to incorporate biocompatible protease and peptidase inhibitors into polypeptide containing formulations.

The concentration of the pharmaceutically active agent in the preparations of this invention will of course depend on the particular agent chosen, on its efficacy, on a comparison of its bioavailability by nasal administration and by other routes of administration, for example parenteral injection, and on the desired frequency of administration combined with the desired single dosage of the formulation. Such pharmacological data can routinely be obtained by the skilled artisan from animal experiments, for example in terms of index values, such as those estimated for insulin preparations in the examples hereinafter provided.

Taking insulin as an example, its concentration in the preparation of this invention may be in the range of from about 5 to 1000 international units (I.U.) per ml, preferably from 50 to 500 I.U. per ml.

The insulin preparations of this invention preferably contain bovine, porcine or human insulin.

An exemplary mode of preparing the insulin preparations of this invention wherein the diluent is water comprises dissolving insulin, for example crystalline zinc insulin, for example the highly purified grade of insulin disclosed in British Patent No. 1,285,023, in water in the presence of an acid, for example hydrochloric acid. An aqueous solution of a preservative, for example phenol, an alkyl phenol, such as cresol, or methyl p-hydroxybenzoate, is prepared separately, optionally also containing an agent rendering the solution isotonic, such as sodium chloride or glycerol. Furthermore, the preservative solution may contain a buffering agent, such as sodium phosphate, sodium citrate, sodium acetate or TRIS (tris(hydroxymethyl)aminomethane) and a protease inhibitor. The resulting preservative solution is then admixed with the acid insulin solution followed by addition of a base, for example a sodium hydroxide solution, to adjust the pH value to neutrality. The phospholipid of formula I, optionally in admixture with the fatty oil, may be added to the insulin solution as a solution or an emulsion which is prepared by dissolving or suspending the phospholipid of formula I in water and and, if necessary, subjecting any suspension to an ultrasonic treatment before mixing with the insulin solution. Alternatively the phospholipid solution or emulsion may, if desired, contain the buffering agent and preservative. After mixing, the pH value of the insulin preparation may be readjusted to neutrality. Finally, the resulting insulin solution is made up to the calculated volume by addition of water.

The preparations of this invention may be used in any dosage dispensing device adapted for intranasal administration. The device should be constructed with a view to ascertaining optimum metering accuracy and compatibility of its constructive elements, such as container, valve and actuator with the nasal formulation and could be based on a mechanical pump system, e.g. that of a metered-dose nebulizer, or on a pressurized aerosol system. The aerosol system requires the propellant to be inert towards the formulation. Suitable propellants may be selected among such gases as fluorocarbons, hydrocarbons, nitrogen and dinitrogen oxide or mixtures thereof.

Further details of practising this invention are furnished by way of the following examples which, however, should not be construed so as to imposes any kind of limitation to the scope of this invention.

The insulin starting material used in Examples 1–12 contained about 20 to 30 µg zinc per mg nitrogen.

Soybean oil and peanut oil were purified grades corresponding to those of U.S.P. XXI and N.F. XVI, respectively.

EXAMPLE 1

772 mg of human insulin were dissolved in 40 ml of 0.02M hydrochloric acid and 1.6 g of anhydrous glycerol were added. Furthermore, distilled water was added to 80 ml. The pH value was adjusted to 7.4 with a 0.2M sodium hydroxide solution 1.0 g of didecanoyl L-α-phosphatidylcholine was dissolved in 2 ml of ethanol (96%) and were via a hypodermic syringe injected into 10 ml of distilled water. The resulting, turbid solution was subjected to ultrasonic treatment with a high energy ultrasound probe for 10 minutes and the resulting colloid solution was added to the insulin solution with stirring and distilled water was added to 100 ml. This preparation, containing 200 I.U./ml of insulin, was dispensed in a spray suitable for nasal administration and 100 microliters were administered to the nasal cavity of male NZW rabbits. A similar preparation, but without didecanoyl L-α-phosphatidylcholine, was also tested in the rabbits.

At fixed time intervals, blood samples were obtained from the marginal ear vein and the glucose concentration determined by a hexokinase method.

The results were:

| | Blood glucose in percent of initial level: | | | | |
|---|---|---|---|---|---|
| Minutes after treatment | 0 | 30 | 60 | 90 | 120 |
| Insulin without additive | 100 | 100 | 103 | 99 | 100 |
| Insulin with didecanoyl L-α-phosphatidyl-choline | 100 | 56 | 65 | 70 | 81 |

EXAMPLE 2

100 mg of didecanoyl L-α-phosphatidylcholine was dissolved in 100 mg of soy bean oil and the solution was added to 5 ml of 0.01M sodium phosphate buffer, pH 7.4.

The mixture was emulsified by ultrasonic treatment; 2 ml of an insulin solution of 400 units per ml were added to the emulsion and pH was adjusted to 7.4 and water added to 10 ml.

After the nasal application of this preparation in rabbits, the blood glucose concentration is monitored for 120 minutes. The area over the curve, where the single blood glucose values are expressed as per cent of the initial value, is estimated by the triangle method. The index is then calculated according to this formula:

$$Index = 0.053 \times A/D$$

wherein A is the area over curve for the test preparation, D is the dose of test preparation, and the factor 0.053 is an emperically derived factor from a subcutaneous application of a fast acting insulin preparation.

Tested in this way the nasal insulin emulsion has an index of 24%.

A similar preparation but made without a vegetable oil has an index of 12–15%.

EXAMPLES 3–12

The preparations of Examples 3–6, 8 and 12 were prepared a manner analogous to that described in Example 1 while the preparations of Example 7 and 9–11 were prepared by the method of Example 2. The following abbreviations are used in the table:
Phosphatidylcholine: PC
Didecanoyl phosphatidylcholine: DDPC
Dilauroyl phosphatidylcholine: DLPC
Percent contents are in weight per volume. All preparations contained 80 I.U./ml of insulin.

| Example No. | Phospholipid | Vegetable oil | Index |
|---|---|---|---|
| 3 | 0.5% lauroyl lysoPC | none | 10.9% |
| 4 | 0.5% myristoyl lysoPC | | 3.8% |
| 5 | 0.5% stearoyl lysoPC | | 0.8% |

| Example No. | Phospholipid | Vegetable oil | Index |
|---|---|---|---|
| 6 | 0.5% DDPC +0.2% lauroyl lysoPC | none | 13.9% |
| 7 | 0.5% DDPC +0.2% lauroyl lysoPC | peanut oil 2% | 21.9% |
| 8 | 0.5% didecyl-O-PC | none | 21.9% |
| 9 | 0.5% didecyl-O-PC +0.5% DDPC | peanut oil 1% | 28.7% |
| 10 | 0.5% DDPC 0.5% DLPC | peanut oil 1% | 18.9% |
| 11 | 0.5% DDPC 0.5% dimyristoyl PC | peanut oil 1% | 14.3% |
| 12 | 0.5% DDPC | none | 11% |

The data show the superior absorption enhancing effects of phosphatidylcholines with medium chain length acyl or alkyl groups.

EXAMPLE 13

100 mg of didecanoyl L-α-phosphatidylcholine was dissolved in 100 mg of soybean oil and the solution was added to 5 ml of 0.01M sodium phosphate buffer, pH 7.4 containing 160 mg of glycerol. After emulsification of the mixture by ultrasonic treatment 100 mg of glucagon was added to the emulsion, pH was adjusted to 7.4 and water was added to 10 ml.

Following nasal application of this preparation to rabbits, the glucose concentration of blood samples drawn from the marginal ear vein was monitored by the hexokinase method.

The following blood glucose concentrations were obtained with time:

| Minutes after treatment | 0 | 15 | 30 | 60 | 120 |
|---|---|---|---|---|---|
| Glucagon without enhancer system | 100 | 107 | 113 | 111 | 107 |
| Glucagon with enhancer system | 100 | 144 | 178 | 188 | 163 |

We claim:

1. A preparation for intranasal administration characterized by containing a pharmaceutically active polypeptide and an absorption enhancing system containing a fatty oil and at least one phospholipid of the formula I

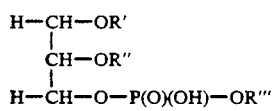

wherein R' and R" are the same or different each representing hydrogen, alkyl, alkenyl, alkylcarbonyl, alkenylcarbonyl, alkadienylcarbonyl, alkatrienylcarbonyl or alkatetraenylcarbonyl containing not more than 14 carbon atoms with the proviso that both R' and R" are not hydrogen, and R''' represents a hydrophilic group selected from the group consisting of 2-(trimethylammonio)ethyl, 2-aminoethyl, 2-carboxy-2-aminoethyl, 2,3-dihydroxypropyl or 2,3,4,5,6-pentahydroxycyclohexyl.

2. The preparation according to claim 1, wherein R''' is 2-(trimethylammonio)ethyl.

3. The preparation of claim 2, wherein each of R' and R" is alkyl or alkylcarbonyl containing from 4 to 12 carbon atoms.

4. The preparation of claim 3, wherein R' and R" each represents nonylcarbonyl.

5. The preparation of claim 2, wherein either R' or R" is hydrogen.

6. The preparation according to claim 1, wherein the fatty oil is a vegetable oil, selected from the group consisting of soybean oil, peanut oil, coconut oil, maize oil, olive oil and sunflower oil.

7. The preparation according to claim 1, wherein the content of phospholipid of formula I is in the range of from 0.01 to 10% (w/v) of the preparation.

8. The preparation according to claim 1, wherein the content of fatty oil is in the range of from 0.01 to 50% (w/v) of the preparation.

9. A preparation for intranasal administration characterized by containing a pharmaceutically active polypeptide and an absorption enhancing system containing from about 0.5-5% w/v of at least one phospholipid of the formula I

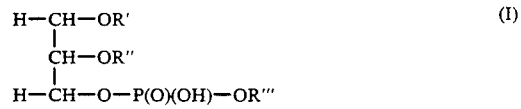

wherein R' and R" are the same or different each representing hydrogen, alkyl, alkenyl, alkylcarbonyl, alkenylcarbonyl, alkadienylcarbonyl, alkatrienylcarbonyl or alkatetraenylcarbonyl containing not more than 14 carbon atoms with the proviso that both R' and R" are not hydrogen, and R''' represents a hydrophilic group selected from the group consisting of 2-(trimethylammonio)ethyl, 2-aminoethyl, 2-carboxy-2-aminoethyl, 2,3-dihydroxypropyl or 2,3,4,5,6-pentahydroxycyclohexyl.

10. The preparation of claim 9, wherein the polypeptide is glucagon.

11. A preparation for intranasal administration characterized by containing insulin, an insulin derivative, a mixture of insulin and at least one insulin derivative, or a mixture of insulin derivatives and an absorption enhancing system containing from about 0.5-5% w/v of at least one phospholipid of the formula I

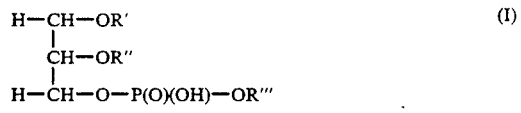

wherein R' and R" are the same or different each representing hydrogen, alkyl, alkenyl, alkylcarbonyl, alkenylcarbonyl, alkadienylcarbonyl, alkatrienylcarbonyl or alkatetraenylcarbonyl containing not more than 14 carbon atoms with the proviso that both R' and R" are not hydrogen, and R''' represents a hydrophilic group selected from the group consisting of 2-(trimethylammonio)ethyl, 2-aminoethyl, 2-carboxy-2-aminoethyl, 2,3-dihydroxypropyl or 2,3,4,5,6-pentahydroxycyclohexyl.

12. A preparation according to claim 11 having an insulin activity content in the range of from 5 to 1000 international units per ml of the preparation.

13. A treatment method which comprises intranasally administering to one in need of treatment a preparation containing a pharmaceutically active peptide and from about 0.1-10% w/v of at least one phospholipid of the formula I

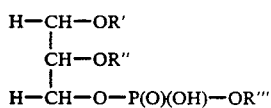

wherein R' and R" are the same or different each representing hydrogen, alkyl, alkenyl, alkylcarbonyl, alkenylcarbonyl, alkadienylcarbonyl, alkatrienylcarbonyl or alkatetraenylcarbonyl containing not more than 14 carbon atoms with the proviso that both R' and R" are not hydrogen, and R''' represents a hydrophilic group selected from the group consisting of 2-(trimethylammonio)ethyl, 2-aminoethyl, 2-carboxy-2-aminoethyl, 2,3-dihydroxypropyl or 2,3,4,5,6-pentahydroxycyclohexyl.

14. The method of claim 13 wherein the preparation further contains a fatty oil.

15. The method of claim 14 wherein the fatty oil is a vegetable oil selected from the group consisting of soybean oil, peanut oil, coconut oil, maize oil, olive oil and sunflower oil.

16. The method of claim 13 wherein the pharmaceutically active peptide is selected from the group consisting of glucagon and insulin or an insulin derivative.

17. A method for treating a diabetic which comprises intranasally administering thereto a preparation containing insulin, an insulin derivative, a mixture of insulin and at least one insulin derivative, or a mixture of insulin derivatives and from about 0.01-10% w/v of at least one phospholipid of the formula I

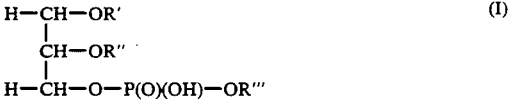

wherein R' and R" are the same or different each representing hydrogen, alkyl, alkenyl, alkylcarbonyl, alkenylcarbonyl, alkadienylcarbonyl, alkatrienylcarbonyl or alkatetraenylcarbonyl containing not more than 14 carbon atoms with the proviso that both R' and R" are not hydrogen, and R''' represents a hydrophilic group selected from the group consisting of 2-(trimethylammonio)ethyl, 2-aminoethyl, 2-carboxy-2-aminoethyl, 2,3-dihydroxypropyl or 2,3,4,5,6-pentahydroxycyclohexyl.

* * * * *